(12) United States Patent
Tachikawa

(10) Patent No.: US 6,175,031 B1
(45) Date of Patent: Jan. 16, 2001

(54) METHOD FOR SYNTHESIZING SILICON COMPOUNDS THAT CONTAIN A SUBSTITUENT BONDED TO SILICON THROUGH A SILICON-CARBON LINKAGE

(75) Inventor: Mamoru Tachikawa, Kanagawa (JP)

(73) Assignee: Dow Corning Asia, Ltd., Tokyo (JP)

(*) Notice: Under 35 U.S.C. 154(b), the term of this patent shall be extended for 0 days.

(21) Appl. No.: 09/519,925

(22) Filed: Mar. 7, 2000

(51) Int. Cl.$^7$ ............................................. C07F 7/08
(52) U.S. Cl. ................................................ 556/479
(58) Field of Search ............................... 556/479

(56) References Cited

U.S. PATENT DOCUMENTS 6,054,602 * 4/2000 Tachikawa ........................ 556/479

* cited by examiner

*Primary Examiner*—Paul F. Shaver
(74) *Attorney, Agent, or Firm*—William F. Boley

(57) ABSTRACT

A method for synthesizing silicon compounds that contain a substituent bonded to silicon through a Si—C bond comprising a platinum-catalyzed hydrosilylation reaction between SiH-substituted silicon compounds and unsaturated group-functional organic compounds or unsaturated group-functional organosilicon compounds and exhibits a high catalyst activity and stability and affords a high positional selectivity in the hydrosilylation reaction product.

12 Claims, No Drawings

METHOD FOR SYNTHESIZING SILICON COMPOUNDS THAT CONTAIN A SUBSTITUENT BONDED TO SILICON THROUGH A SILICON-CARBON LINKAGE

BACKGROUND OF INVENTION

This invention relates to a method for synthesizing silicon compounds that contain a substituent bonded to silicon through Si—C bond. This method is undertaken for the purposes of property improvement and imparting reactivity and proceeds through the reaction of unsaturated compounds with silane compounds.

The hydrosilylation reaction is a generally applicable method for the chemical modification of organic compounds by silane compounds. This method employs hydrosilylation between SiH-functional silane and an unsaturated bond-bearing organic compound and is applicable to a fairly broad range of SiH-functional compounds and unsaturated bond-bearing organic compounds. Platinum and rhodium catalysts are generally used to run the hydrosilylation reaction in industrial or commercial processes. Since these metals are very expensive, it is crucial that the catalytic efficiency in the hydrosilylation reaction also be very high. In addition, the hydrosilylation reaction is frequently accompanied by competing side reactions and may include reaction pathways that produce a number of isomers. As a consequence, the hydrosilylation reaction is generally accompanied by such catalyst-related issues as product yield, product selectivity, and production of a single isomer. Modification of the catalyst can be carried out in order to address these problems and issues. For example, various ligands can be added and/or chemically bonded to the catalyst, or the catalyst can be immobilized on any of various different supports. However, these chemical and physical modifications are typically problematic, for example, (1) their effects may rapidly disappear and (2) an improved catalytic selectivity is generally accompanied by a lower activity. In addition, since platinum catalysts gradually lose their activity under oxygen-free conditions, implementation of the hydrosilylation reaction in the presence of oxygen becomes unavoidable thereby increasing side reactions and risk of fire.

With regard to the platinum-catalyzed hydrosilylation reaction between SiH-functional silicon compounds and unsaturated group-bearing organic compounds, the object of the present invention is to introduce a reaction method that provides a high catalyst activity and stability and that also provides a high positional selectivity in the hydrosilylation reaction product. An additional object is to achieve these features without the addition of oxygen and thereby reduce the risk of fire and explosion in the hydrosilylation reaction.

SUMMARY OF INVENTION

A method for synthesizing silicon compounds containing a substituent bonded to silicon through a Si—C bond comprising reacting (a) an unsaturated group-functional organic compound or unsaturated group-functional organosilicon compound with (b) a hydrosilyl-functional organosilicon compound described by formula $$HSiR^2_nZ_{3-n}$$

under the action of (c) a platinum catalyst and in the presence of (d) a hydro(acyloxy)-functional silicon compound described by formula $$HSiR_2(O(C=O)R^1)$$

or in the presence of (e) a carboxylic acid compound and a hydro(alkoxy)silane; where each R is independently selected from the group consisting of organic groups, siloxy groups, and siloxanoxy groups and each $R^1$ is independently selected from the group consisting of a hydrogen atom and organic groups, each $R^2$ is an independently selected hydrocarbon group; each Z is independently selected from the group consisting of silamino groups, siloxy groups, and siloxanoxy groups, and n=0, 1, 2, or 3.

DESCRIPTION OF INVENTION

The present invention is a method for synthesizing silicon compounds that contain a substituent bonded to silicon through a the Si—C bond by reacting (a) an unsaturated group-functional organic compound or unsaturated group-functional organosilicon compound with (b) a hydrosilyl-functional organosilicon compound described by formula $$HSiR^2_nZ_{3-n}$$

under the action of (c) a platinum catalyst and in the presence of (d) a hydro(acyloxy)-functional silicon compound described by formula $$HSiR_2(O(C=O)R^1)$$

or in the presence of (e) a carboxylic acid compound and a hydro(alkoxy)silane; where each R is independently selected from the group consisting of organic groups, siloxy groups, and siloxanoxy groups, each $R^1$ is independently selected from the group consisting of the hydrogen atom and organic groups, each $R^2$ is an independently selected hydrocarbon group; each Z is independently selected from the group consisting of silamino groups, siloxy groups, and siloxanoxy groups; and n=0, 1, 2, or 3.

The following compounds (1) through (8) are examples of preferred unsaturated compounds encompassed by component (a):

(1) styrene and styrene derivatives;
(2) vinylsilane compounds;
(3) siloxane compounds containing the vinyl group directly bonded to silicon;
(4) epoxy-functional olefins;
(5) diene compounds;
(6) allyl compounds defined by $CH_2=CHCH_2X$ where X=halogen, alkoxy, or acyloxy;
(7) vinyl-functional olefin compounds; and
(8) acetylenic compounds.

While the unsaturated compounds encompassed by component (a) are preferably selected from compounds (1) to (8) as defined above, the unsaturated compound (a) may contain atoms other than carbon and hydrogen in its structure, the other atoms being selected from the group consisting of O, N, F, Cl, Br, Si, and S. However, compound (6) remains as described above.

The styrene and styrene derivatives can be exemplified by styrenic hydrocarbons such as styrene, p-methylstyrene, p-ethylstyrene, p-phenylstyrene, and divinylbenzene; halogenated styrenes such as p-fluorostyrene, p-chlorostyrene, p-bromostyrene, p-iodostyrene, p-(chloromethyl)styrene, and m-(chloromethyl)styrene; oxygenated styrene derivatives and silicon-containing styrene derivatives such as p-methoxystyrene and p-trimethylsilylstyrene; nitrogenous styrene derivatives such as p-(diphenylamino)styrene, p-(ditolylamino)styrene, p-(dixylylamino)styrene, and bis (4-vinylphenyl)(4-methylphenyl)amine.

The vinylsilane compounds and siloxane compounds containing the vinyl group directly bonded to silicon can be exemplified by vinyltrialkylsilanes such as vinyltrimethylsilane, vinyltriethylsilane, vinyltripropylsilane, and vinyldimethylethylsilane; vinylalkoxysilanes such as vinyltrimethoxysilane, vinyltriethoxysilane, vinylmethyldiethoxysilane, and vinyldimethylmethoxysilane; vinyl-functional siloxanes such as 1,3-divinyltetramethyldisiloxane, α,ω-divinylpolydimethylsiloxanes, and 1,3,5,7-tetravinyl-1,3,5,7-tetramethylcyclotetrasiloxane; and vinyl-functional silazanes such as 1,3-divinyltetramethyldisilazane and 1,3,5,7-tetravinyl-1,3,5,7-tetramethylcyclotetrasilazane.

The epoxy-functional olefins can be exemplified by allyl glycidyl ether and vinylcyclohexene oxide. The diene compounds can be exemplified by 1,3-butadiene, isoprene, 1,5-hexadiene, 1,3-octadiene, and 1,3-cyclohexadiene. The allyl compound $CH_2=CHCH_2X$ can be exemplified by allyl chloride, allyl acetate, and allyl methacrylate.

The vinyl-functional olefin compounds may be straight chain or branched and may contain an aromatic hydrocarbon group as a substituent. The straight-chain unsaturated olefin compounds can be exemplified by ethylene, propylene, 1-butene, 1-hexene, 1-octene, and 1-octadecene. The branched unsaturated olefin compounds can be exemplified by isobutylene, 3-methyl-1-butene, 3,5-dimethyl-1-hexene, and 4-ethyl-1-octene.

Olefin compounds containing an atom or atoms from the group consisting of O, N, F, Cl, Br, Si, and S are exemplified by oxygenated allyl compounds such as allyl methacrylate; vinyl-functional amine compounds such as N-vinylcarbazole; halogenated olefins such as 4-chloro-1-butene and 6-bromo-1-hexene; Si-functional olefin compounds such as allyloxytrimethylsilane; and sulfur-containing olefin compounds such as allyl mercaptan and allyl sulfide. Allylbenzene and 4-phenyl-1-butene are examples of aromatic hydrocarbon group-containing olefin compound.

The acetylenic compound may contain the terminal ethynyl group ($CH\equiv C-$) or may contain the ethynylene group ($-C\equiv C-$) in an internal position in the molecule. The acetylenic compound can also contain aromatic hydrocarbyl as a substituent.

The following are examples of acetylenic compounds containing the terminal ethynyl group ($CH\equiv C-$) :acetylene, propyne, 1-butyne, 1-hexyne, and 1-octyne. The following are examples of acetylenic compounds containing the ethynylene ($-C\equiv C-$) group in an internal position in the molecule:2-butyne, 2-hexyne, 3-hexyne, and 4-octyne. The aromatic hydrocarbyl-substituted acetylenic compound can be exemplified by phenylacetylene, 3-phenylpropyne, and 4-phenyl-1-butyne. Acetylenic compounds containing an atom or atoms selected from the group consisting of O, N, F, Cl, Br, Si, and S can be exemplified by oxygenated acetylenic compounds such as 3-methyl-1-butyn-3-ol and 3-phenyl-1-butyn-3-ol; silicon-containing acetylenic compounds such as O-trimethylsilylated 3-methyl-1-butyn-3-ol ($HC\equiv C-C(CH_3)_2-O-Si(CH_3)_3$) and O-trimethylsilylated 3-phenyl-1-butyn-3-ol ($HC\equiv C-C$$(CH_3)(C_6H_5)-O-Si(CH_3)_3$); and halogenated acetylenic compounds such as propargyl chloride and propargyl bromide.

The hydrosilyl-functional organosilicon compound (b) is a Si—H functional silicon compound described by formula $$HSiR^2_nZ_{3-n} \qquad (2)$$

in which n=0, 1, 2, or 3; each $R^2$ is an independently selected hydrocarbon group; and each Z is independently selected from the group consisting of silamino groups, siloxy groups, and siloxanoxy groups.

The compound (b) can be specifically exemplified by $HSiR^2_3$, in which the hydrocarbyl group $R^2$ can be selected from the group consisting of alkyl, aryl, and aralkyl. Representative compounds include, for example, trialkylsilanes such as trimethylsilane, dimethylethylsilane, and dimethylhexylsilane; triarylsilanes such as triphenylsilane; triaralkylsilanes such as tribenzylsilane; dialkylarylsilanes such as dimethylphenylsilane; dialkylaralkylsilanes such as dimethylbenzylsilane; and monoalkyldiarylsilanes such as methyldiphenylsilane.

In the case of $HSiR^2_2Z$, compounds in which Z=silamino, such compounds are exemplified by pentamethyldisilazane and 1,1,3,3-tetramethyldisilazane. Compounds in which Z=siloxy are exemplified by pentamethyldisiloxane and 1,1,3,3-tetramethyldisiloxane. Compounds in which Z=siloxanoxy are exemplified by 1,1,3,3,5,5,5-heptamethyltrisiloxane, 1,1,3,3,5,5-hexamethyltrisiloxane, 1,3,5-trimethyl-1,3,5-triphenyltrisiloxane, polydimethylsiloxane having Si—H at a single terminal, polydimethylsiloxane having Si—H at both terminals, and branched siloxanes bearing dimethylsilyl terminals such as methyltris (dimethylsiloxy)silane, n-propyltris(dimethylsiloxy)silane, and tetrakis(dimethylsiloxy)silane.

In the case of $HSiR^2Z_2$, compounds in which Z=silamino can be exemplified by 1,1,1,3,5,5,5-heptamethyltrisilazane; compounds in which Z=siloxy can be exemplified by 1,1,1,3,5,5,5-heptamethyltrisiloxane and 1,1,3,5,5-pentamethyltrisiloxane; and compounds in which Z=siloxanoxy can be exemplified by 1,1,1,3,3,5,7,7,9,9,9-undecamethylpentasiloxane, polymethylhydrogensiloxane functionalized with trimethylsilyl at both terminals, methylhydrogensiloxane-dimethylsiloxane copolymer functionalized with trimethylsilyl at both terminals, and polymethylhydrogensiloxane functionalized with Si—H at both terminals.

In the case of $HSiZ_3$, compounds in which Z=siloxy can be specifically exemplified by tris(trimethylsiloxy)silane and octakis(hydrogensilsesquioxane), while compounds in which Z=siloxanoxy can be exemplified by tris (trimethylsilyldimethylsiloxanoxy)silane.

The hydro(acyloxy)-functional silicon compound (d) used by this invention is described by formula

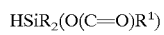
$$HSiR_2(O(C=O)R^1)$$

in which R is preferably selected from $C_1$ to $C_6$ hydrocarbyl groups and $C_1$ to $C_6$ alkoxy groups and $R^1$ is preferably hydrogen or a saturated or unsaturated hydrocarbon group that contains from 1 to 20 carbons and that may contain at least 1 atom selected from the group consisting of oxygen, halogen, sulfur, and silicon. This group R can be exemplified by methyl, ethyl, n-propyl, isopropyl, phenyl, methoxy, ethoxy, n-propoxy, and isopropoxy. The group $R^1$ can be exemplified by methyl, ethyl, n-propyl, isopropyl, and phenyl.

The following are examples of R for R=siloxy and R=siloxanoxy. For the case of R=siloxy, R can is exemplified by trimethylsiloxy, triethylsiloxy, phenyldimethylsiloxy, diphenylmethylsiloxy, and (3,3,3-trifluoropropyl)dimethylsiloxy. For the case of R=siloxanoxy, R can be exemplified by groups having a polydimethylsiloxane structure for the main chain and a siloxy group structure such as trimethylsiloxy for the terminal or a terminal endblocked by —SiH(CH$_3$)(OC(=O)CH$_3$). Viewed from the perspective of obtaining a practical reaction rate, the siloxane unit degree of polymerization (number-average degree of polymerization) in the siloxanoxy group should not exceed 1,000 and more preferably not exceed 500.

The hydro(acyloxy)-functional silicon compound used in the present invention can be exemplified by hydroformyloxysilanes, hydroacetoxysilanes, hydropropionyloxysilanes, hydrobutyryloxysilanes, hydrolauroyloxysilanes, hydrostearoyloxysilanes, hydrobenzoyloxysilanes, hydrochloroacetoxysilanes, hydrodichloroacetoxysilanes, hydrotrichloroacetoxysilanes, hydrotrifluoroacetoxysilanes, and hydrobenzyloylsilanes.

At a more specific level, this hydro(acyloxy)silane can be exemplified by hydroformyloxysilanes such as dimethylformyloxysilane, diethylformyloxysilane, methylphenylformyloxysilane, methylmethoxyformyloxysilane, methylethoxyformyloxysilane, methylisopropoxyformyloxysilane, and diphenylformyloxysilane; hydroacetoxysilanes such as dimethylacetoxysilane, diethylacetoxysilane, methylphenylacetoxysilane, methylmethoxyacetoxysilane, methylethoxyacetoxysilane, methylisopropoxyacetoxysilane, and diphenylacetoxysilane; hydropropionyloxysilanes such as dimethylpropionyloxysilane, diethylpropionyloxysilane, methylphenylpropionyloxysilane, methylmethoxypropionyloxysilane, methylethoxypropionyloxysilane, methylisopropoxypropionyloxysilane, and diphenylpropionyloxysilane; hydrobutyryloxysilanes such as dimethylbutyryloxysilane, diethylbutyryloxysilane, methylphenylbutyryloxysilane, methylmethoxybutyryloxysilane, methylethoxybutyryloxysilane, methylisopropoxybutyrylsilane, and diphenylbutyryloxysilane; hydrolauroyloxysilanes such as dimethyllauroyloxysilane, methylphenyllauroyloxysilane, diphenyllauroyloxysilane, methylmethoxylauroyloxysilane, and methylethoxylauroyloxysilane; hydrostearoyloxysilanes such as dimethylstearoyloxysilane, methylphenylstearoyloxysilane, diphenylstearoyloxysilane, methylmethoxystearoyloxysilane, and methylethoxystearoyloxysilane; hydrobenzoyloxysilanes such as dimethylbenzoyloxysilane, methylphenylbenzoyloxysilane, diphenylbenzoyloxysilane, methylmethoxybenzoyloxysilane, and methylethoxybenzoyloxysilane; hydrochloroacetoxysilanes such as dimethylchloroacetoxysilane, methylphenylchloroacetoxysilane, diphenylchloroacetoxysilane, methylmethoxychloroacetoxysilane, and methylethoxychloroacetoxysilane; hydrodichloroacetoxysilanes such as dimethyldichloroacetoxysilane, methylphenyldichloroacetoxysilane, diphenyldichloroacetoxysilane, methylmethoxydichloroacetoxysilane, and methylethoxydichloroacetoxysilane; hydrotrichloroacetoxysilanes such as methylphenyltrichloroacetoxysilane, diphenyltrichloroacetoxysilane, methylmethoxytrichloroacetoxysilane, and methylethoxytrichloroacetoxysilane; hydrotrifluoroacetoxysilanes such as dimethyltrifluoroacetoxysilane, methylphenyltrifluoroacetoxysilane, diphenyltrifluoroacetoxysilane, methylmethoxytrifluoroacetoxysilane, and methylethoxytrifluoroacetoxysilane; and hydrobenzoyloxysilanes such as dimethylbenzoyloxysilane, methylphenylbenzoyloxysilane, diphenylbenzoyloxysilane, methylmethoxybenzoyloxysilane, and methylethoxybenzoyloxysilane.

All or a portion of component (d) can be substituted with component (e) which comprises a carboxylic acid compound (e1) and a hydro(alkoxy)silane (e2). The carboxylic acid compound (e1) is preferably selected from carboxylic acids with the following formula (1), carboxylic acid anhydrides with the following formula (2), and silyl carboxylate esters with the following formula (3).

$$R^4COOH \tag{1}$$

$$(R^4CO)_2O \tag{2}$$

$$(R^4COO)_mSiR^5_{4-m}. \tag{3}$$

$R^4$ in the preceding formulas is a substituent selected from the group consisting of hydrogen atoms and saturated and unsaturated hydrocarbon groups that contain from 1 to 20 carbons and that may optionally contain at least 1 atom selected from the group consisting of oxygen, halogen, sulfur, and silicon; each $R^5$ is an independently selected saturated or unsaturated hydrocarbon group containing from 1 to 20 carbons and that optionally may contain at least 1 atom selected from the group consisting of oxygen, halogen, sulfur, and silicon; and m is 1, 2, 3, or 4.

The carboxylic acids encompassed by the carboxylic acid compound (e1) are exemplified by formic acid, acetic acid, monochloroacetic acid, dichloroacetic acid, trichloroacetic acid, trifluoroacetic acid, propionic acid, acrylic acid, methacrylic acid, trimethylacetic acid, cyclohexanoic acid, lauric acid, stearic acid, benzoic acid, toluic acid, p-chlorobenzoic acid, terephthalic acid, and trimesic acid.

The carboxylic acid anhydrides encompassed by the carboxylic acid compound (e1) are exemplified by formic anhydride, acetic anhydride, propionic anhydride, butyric anhydride, lauric anhydride, stearic anhydride, phthalic anhydride, pyromellitic anhydride, and benzoic anhydride.

The silyl carboxylate esters encompassed by the carboxylic acid compound (e1) are exemplified by the esters of formic acid such as trimethylformyloxysilane, dimethyldiformyloxysilane, methyltriformyloxysilane, ethyltriformyloxysilane, phenyltriformyloxysilane, and tetraformyloxysilane; the esters of acetic acid, such as trimethylacetoxysilane, dimethyldiacetoxysilane, methyltriacetoxysilane, methyldiacetoxysilane, triacetoxysilane, ethyltriacetoxysilane, phenyltriacetoxysilane, and tetraacetoxysilane; and the esters of propionic acid such as trimethylpropionyloxysilane, dimethyldipropionyloxysilane, methyltripropionyloxysilane, methyldipropionyloxysilane, tripropionyloxysilane, ethyltripropionyloxysilane, phenyltripropionyloxysilane, and tetrapropionyloxysilane. The carboxylic acid moiety in the silyl carboxylate ester can also be a dicarboxylic acid or tricarboxylic acid.

The hydro(alkoxy)silane (e2) preferably has the following formula (4)

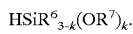

$$HSiR^6_{3-k}(OR^7)_k.$$

in which each $R^6$ is independently selected from $C_1$ to $C_6$ saturated and unsaturated hydrocarbyl groups and each $R^7$ is independently selected from saturated and unsaturated hydrocarbon groups that contain from 1 to 10 carbons and may contain at least 1 atom selected from the group consisting of oxygen, halogen, and silicon, and k=1, 2, or 3.

The hydro(alkoxy)silane (e2) is exemplified by hydromonoalkoxysilanes, hydrodialkoxysilanes, and hydrotrialkoxysilanes. The hydromonoalkoxysilanes are exemplified by dimethylmethoxysilane, dimethylethoxysilane, dimethylpropoxysilane, dimethylisopropoxysilane, dimethyl-n-butoxysilane, dimethyl-n-hexyloxysilane, dimethyl-n-octyloxysilane, dimethyl(2-methoxyethoxy) silane, and dimethyl(2,2,2-trifluoroethoxy)silane. The hydrodialkoxysilanes are exemplified by methyldimethoxysilane, methyldiethoxysilane, methyldipropoxysilane, methyldiisopropoxysilane, ethyldimethoxysilane, ethyldiethoxysilane, phenyldimethoxysilane, and phenyldiethoxysilane. The hydrotrialkoxysilanes can be exemplified by trimethoxysilane, triethoxysilane, tripropoxysilane, and tributoxysilane.

The ranges of the addition ratios recommended for components (d) and (e) are as follows. Component (d) should be added in a quantity that will give a (hydro(acyloxy)-functional silicon compound (d)):(hydrosilyl-functional organosilicon compound (b)) weight ratio of 0.01:1 to 1:1. Component (d) should generally be added in these proportions for the following reasons: at a component (d) ratio below 0.01:1, the effects relative to product selectivity and product yield become unsatisfactory; ratios in excess of 1:1, while still accruing the advantageous effects of this invention, also result in starting material losses.

A (carboxylic acid compound+hydro(alkoxy)silane (e)): (hydrosilyl-functional organosilicon compound (b)) weight ratio of 0.01:1 to 1:100 is also recommended. Component (e) should generally be added in these proportions for the following reasons: at a component (e) ratio below 0.01:1, the effects relative to product selectivity and product yield become unsatisfactory; ratios in excess of 1:1, while still accruing the advantageous effects of this invention, also result in starting material losses The carboxylic acid compound (e1):hydro(alkoxy)silane (e2) ratio in component (e) should generally fall in the range of 0.01:1 to 1:1 as the molar ratio. The advantageous effects of this invention with respect to product selectivity and product yield are unsatisfactory when the carboxylic acid compound is used below this range. The same problem occurs when the carboxylic acid compound is used in excess of the specified range.

The hydrosilylation catalyst used in this invention is specifically exemplified by olefin complexes of zero-valent platinum, vinylsiloxane complexes of zero-valent platinum, halogenated olefin complexes of divalent platinum, chloroplatinic acid, platinum-on-carbon, and platinum-on-silica. The catalyst is not, however, limited to these examples, and in addition to these examples those catalysts in general industrial or commercial use can be used as the subject catalyst.

The reaction temperature should be from 10° C. (inclusive) to 250° C. (inclusive). A range from 20° C. to 200° C. is optimal based on such considerations as achieving a suitable reaction rate, product stability, and stability of the substrate participating in the reaction.

The use of solvent in this invention is not absolutely necessary, but a hydrocarbon compound can be used as a reaction solvent or as a solvent for the catalyst for such purposes as dissolving the substrates, facilitating control of the temperature in the reaction system, and facilitating addition of the catalyst. Solvents optimal for these purposes are saturated and unsaturated hydrocarbon compounds, for example, hexane, cyclohexane, heptane, octane, dodecane, benzene, toluene, xylene, and dodecylbenzene; and halogenated hydrocarbons such as chloroform, methylene chloride, chlorobenzene, and ortho-dichlorobenzene.

The invention will now be explained in greater detail by the following working examples, but this invention is not limited to or by these examples.

In the examples, GC stands for gas chromatography and GC-MS stands for gas chromatography-mass spectroscopy Me is an abbreviation for the methyl group and OAc is an abbreviation for the acetoxy group.

The acyloxysilane, alkylsilane, and siloxane compounds used in the examples were either obtained by purchase or were synthesized by known methods. The unsaturated compounds were obtained by purchase and were used as obtained.

Reference Example 1

Synthesis of Dimethylacetoxysilane 6.5 g Lithium acetate were introduced into a 50-mL flask containing a magnetic stirring bar. This was followed by the gradual addition of 9.2 g dimethylchlorosilane and then stirring overnight at room temperature. An additional 1 g lithium acetate was then added with stirring for another hour. The volatiles were subsequently collected under a vacuum in a dry ice trap. The resulting crude product was distilled at ambient pressure to give a component boiling at 91 to 92° C. The product was confirmed by GC-MS analysis. HMe$_2$SiOAc (m/z (relative intensity)): 117 (6.2), 103 (51.9), 75 (56.2), 61 (100), 59 (23.1), 47 (8.6), 45 (30.3).

EXAMPLE 1

Platinum-Catalyzed Reaction of Styrene and 1,1,3, 3-Tetramethyldisiloxane in the Presence of Dimethylacetoxysilane 252 mg Styrene, 91 mg 1,1,3,3-tetramethyldisiloxane, and 64 mg toluene were placed in a nitrogen-purged glass tube. This was followed by the addition of 9 mg dimethylacetoxysilane and 0.002 mL of a toluene solution (platinum content=0.4 weight %) of a zero-valent platinum complexed with divinylsiloxane. The tube was then sealed with Teflon® tape and a rubber septum and heated for 2 hours in an oil bath at 60° C. After cooling, GC analysis of the product showed the following: the 1,1,3,3-tetramethyldisiloxane had been consumed; the styrene:1,1,3,3-tetramethyldisiloxane 2:1 adduct had been produced in a yield of 93%; and the α,α-adduct:α,β-adduct:β,β-adduct ratio was 1:16:95.

EXAMPLE 2

Platinum-Catalyzed Reaction of Vinyltrimethoxysilane and 1,1,3,3-Tetramethyldisiloxane in the Presence of Dimethylacetoxysilane 280 mg Vinyltrimethoxysilane and 381 mg 1,1,3,3-tetramethyldisiloxane were placed in a nitrogen-purged glass tube. This was followed by the addition of 28 mg dimethylacetoxysilane and 0.005 mL of a toluene solution (platinum content=0.04 weight %) of a zero-valent platinum complexed with divinylsiloxane. The tube was then sealed with Teflon® tape and a rubber septum and heated for 1 hour in an oil bath at 80° C. After cooling, GC analysis of the product showed the following: the vinyltrimethoxysilane had been consumed; the vinyltrimethoxysilane:1,1,3,3-tetramethyldisiloxane 1:1 adduct had been produced in a yield of 71%; and the α-adduct:β-adduct ratio was 1:5.7.

EXAMPLE 3

Platinum-Catalyzed Reaction of Vinyltrimethoxysilane and Tris(Dimethylsiloxy)-N-Propylsilane in the Presence of Dimethylacetoxysilane 362 mg Vinyltrimethoxysilane and 362 mg tris(dimethylsiloxy)-n-propylsilane were placed in a nitrogen-purged glass tube. This was followed by the addition of 27 mg dimethylacetoxysilane and 0.005 mL of a toluene solution (platinum content=0.04 weight %) of a zero-valent platinum complexed with divinylsiloxane. The tube was then sealed with Teflon® tape and a rubber septum and heated for 1 hour in an oil bath at 80° C. After cooling, GC analysis of the product showed the following: the starting materials had been entirely consumed; the vinyltrimethoxysilane:tris(dimethylsiloxy)-n-propylsilane 1:1 adduct, 2:1 adduct, and 3:1 adduct were produced at 1:6:1 as the GC-FID (FID=flame ionization detector) area ratio; and the α-hydrosilylation:β-hydrosilylation ratio in these products was 1:7.1.

Results of GC-MS (EI mode) analysis of the product:
1:1 adduct (MW=444)
α-adduct (z/m (relative intensity)): 59 (37), 73 (49), 179 (26), 193 (35), 207 (28), 251 (12), 295 (28), 311 (38), 339 (100), 353 (11), 401 (23), 429 (22)
β-adduct (z/m (relative intensity)): 59 (57), 73 (95), 89 (22), 91 (18), 101 (31), 121 (21), 179 (64), 193 (86), 207 (80), 221 (25), 235 (24), 251 (15), 279 (15), 295 (100), 311 (39), 323 (16), 339 (24), 353 (8.3), 401 (2.9), 429 (7.8)
2:1 adduct (MW=592)
mixture (z/m (relative intensity): 59 (14), 73 (15), 75 (11), 89 (15), 91 (12), 105 (5.1), 121 (15), 207 (100), 251 (22), 279 (20), 323 (23), 353 (55), 443 (17), 469 (1.9), 503 (2.5), 531 (1.3)
3:1 adduct (MW=740)
β,β,β-adduct (z/m (relative intensity)): 59 (8.2), 73 (6.0), 75 (9.1), 89 (11), 91 (7.9), 121 (11), 207 (90), 279 (7.4), 281 (11), 353 (100), 399 (2.6), 425 (3.2), 471 (2.6), 499 (9.6), 545 (4.6)
α,β,β-adduct (z/m (relative intensity)): 59 (12), 73 (7.3), 75 (12), 89 (15), 91 (11), 121 (13), 207 (100), 279 (7.8), 281 (11), 353 (98), 399 (11), 425 (2.2), 471 (1.6), 487 (1.8), 499 (5.2)
α,α,β-adduct (z/m (relative intensity)): 59 (14), 73 (61), 75 (17), 89 (17), 91 (9.5), 105 (7.6), 121 (10), 147 (19), 207 (100), 221 (16), 223 (13), 281 (22), 353 (93), 355 (36), 399 (16), 429 (20), 487 (10), 499 (16), 545 (30)

EXAMPLE 4

Platinum-Catalyzed Reaction of Styrene and 1,1,3,3-Tetramethyldisiloxane in the Presence of Triethoxysilane and Acetic Acid 928 mg Styrene, 426 mg 1,1,3,3-tetramethyldisiloxane, and 348 mg triethoxysilane were placed in a nitrogen-purged glass tube. This was followed by the addition of 10 mg acetic acid and 0.009 mL of a toluene solution (platinum content=0.04 weight %) of a zero-valent platinum complexed with divinylsiloxane. The reaction tube was then sealed with Teflon® tape and a rubber septum and heated for 2 hours in an oil bath at 80° C. After cooling, GC analysis of the product showed the following: the triethoxysilane and 1,1,3,3-tetramethyldisiloxane had been almost entirely consumed (>98%); the styrene:1,1,3,3-tetramethyldisiloxane 2:1 adduct had been produced in a yield of 96%; the styrene:triethoxysilane 1:1 adduct had been produced in a yield of 97%; the α,β-adduct:β,β-adduct ratio for the former was 1:19; and the α-adduct:β-adduct ratio for the latter was 1:185.

Comparative Example 1

Platinum-Catalyzed Reaction of Styrene and 1,1,3,3-Tetramethyldisiloxane in the Absence of Both Component (d) and Component (e)

252 mg Styrene, 91 mg 1,1,3,3-tetramethyldisiloxane, and 64 mg toluene were placed in a nitrogen-purged glass tube. This was followed by the addition of 0.002 mL of a toluene solution (platinum content=0.4 weight %) of a zero-valent platinum complexed with divinylsiloxane. The tube was then sealed with Teflon® tape and a rubber septum and heated for 2 hours in an oil bath at 60° C. After cooling, GC analysis of the product showed the following: the 1,1,3,3-tetramethyldisiloxane had been consumed; the styrene:1,1,3,3-tetramethyldisiloxane 2:1 adduct had been produced in a yield of 92%; and the α,α-adduct:α,β-adduct:β,β-adduct ratio was 1:4.2:5.8.

Comparative Example 2

Platinum-Catalyzed Reaction of Styrene and 1,1,3,3-Tetramethyldisiloxane in the Presence of Trimethylacetoxysilane and Absence of Hydro(Alkoxy)Silane 252 mg Styrene, 91 mg 1,1,3,3-tetramethyldisiloxane, and 64 mg toluene were placed in a nitrogen-purged glass tube. This was followed by the addition of 0.01 mL trimethylacetoxysilane and 0.002 mL of a toluene solution (platinum content=0.4 weight %) of a zero-valent platinum complexed with divinylsiloxane. The tube was then sealed with Teflon® tape and a rubber septum and heated for 2 hours in an oil bath at 60° C. After cooling, GC analysis of the product showed the following: the 1,1,3,3-tetramethyldisiloxane had been consumed; the styrene:1,1,3,3-tetramethyldisiloxane 2:1 adduct had been produced in a yield of 93%; and the α,α-adduct:α,β-adduct:β,β-adduct ratio was 1:4.2:5.7.

Comparative Example 3

Platinum-Catalyzed Reaction of Styrene and 1,1,3,3-Tetramethyldisiloxane in the Presence of Ethyltriacetoxysilane and Absence of Hydro(Alkoxy)Silane 252 mg Styrene, 91 mg 1,1,3,3-tetramethyldisiloxane, and 64 mg toluene were placed in a nitrogen-purged glass tube. This was followed by the addition of 0.005 mL ethyltriacetoxysilane and 0.002 mL of a toluene solution (platinum content=0.4 weight %) of a zero-valent platinum complexed with divinylsiloxane. The tube was then sealed with Teflon® tape and a rubber septum and heated for 2 hours in an oil bath at 60° C. After cooling, GC analysis of the product showed the following: the 1,1,3,3-tetramethyldisiloxane had been consumed; the styrene:1,1,3,3-tetramethyldisiloxane 2:1 adduct had been produced in a yield of 93%; and the α,α-adduct:α,β-adduct:β,β-adduct ratio was 1:4.3:6.3.

Comparative Example 4

Platinum-Catalyzed Reaction of Vinyltrimethoxysilane and 1,1,3,3-Tetramethyldisiloxane in the Absence of Both Components (d) and (e)

280 mg Vinyltrimethoxysilane and 381 mg 1,1,3,3-tetramethyl-1,3-disiloxane were placed in a nitrogen-purged glass tube. This was followed by the addition of 0.005 mL of a toluene solution (platinum content=0.04 weight %) of a zero-valent platinum complexed with divinylsiloxane. The tube was then sealed with Teflon® tape and a rubber septum and heated for 1 hour in an oil bath at 80° C. After cooling, GC analysis of the product showed the following: the vinyltrimethoxysilane had been consumed; the vinyltrimethoxysilane:1,1,3,3-tetramethyl-1,3-disiloxane 1:1 adduct had been produced in a yield of 72%; and the α-adduct:β-adduct ratio was 1:2.0.

Comparative Example 5

Platinum-Catalyzed Reaction of Vinyltrimethoxysilane and Tris(Dimethylsiloxy)-N-Propylsilane in the Absence of Both Components (d) and (e)

362 mg Vinyltrimethoxysilane and 362 mg tris (dimethylsiloxy)-n-propylsilane were placed in a nitrogen-purged glass tube. This was followed by the addition of 0.005 mL of a toluene solution (platinum content=0.04 weight %) of a zero-valent platinum complexed with divinylsiloxane. The tube was then sealed with Teflon® tape and a rubber septum and heated for 1 hour on an oil bath at 80° C. After cooling, GC analysis of the product showed the following: the starting materials had been entirely consumed; the vinyltrimethoxysilane:tris(dimethylsiloxy)-n-propylsilane 1:1 adduct, 2:1 adduct, and 3:1 adduct were produced at 1:4.9:3.4 as the GC (FID) area ratio; and the α-hydrosilylation:β-hydrosilylation ratio in these products was 1:2.4.

Comparative Example 6

Platinum-Catalyzed Reaction of Styrene and 1,1,3,3-Tetramethyldisiloxane in the Presence of Triethoxysilane and Absence of a Carboxylic Acid Compound 928 mg Styrene, 426 mg 1,1,3,3-tetramethyldisiloxane, and 348 mg triethoxysilane were placed in a nitrogen-purged glass tube. This was followed by the addition of 0.009 mL of a toluene solution (platinum content=0.04 weight %) of a zero-valent platinum complexed with divinylsiloxane. The tube was then sealed with Teflon® tape and a rubber septum and heated for 2 hours in an oil bath at 80° C. After cooling, GC analysis of the product showed the following: 84% of the 1,1,3,3-tetramethyldisiloxane had been consumed; 31% of the triethoxysilane had been consumed; the styrene:1,1,3,3-tetramethyldisiloxane 2:1 adduct had been produced in a yield of 51%; the styrene: triethoxysilane 1:1 adduct had been produced in a yield of 28%; the α,α-adduct:α,β-adduct:β,β-adduct ratio for the former was 1:6.5:13.9; and the α-adduct:β-adduct ratio for the latter was 1:6.

I claim:
1. A method for synthesizing silicon compounds containing a substituent bonded to silicon through a Si—C bond comprising reacting (a) an unsaturated group-functional organic compound or unsaturated group-functional organosilicon compound with (b) a hydrosilyl-functional organosilicon compound described by formula

$$HSiR^2_n Z_{3-n}$$

under the action of (c) a platinum catalyst and in the presence of (d) a hydro(acyloxy)-functional silicon compound described by formula $$HSiR_2(O(C=O)R^1)$$

or in the presence of (e) a carboxylic acid compound and a hydro(alkoxy)silane; where each R is independently selected from the group consisting of organic groups, siloxy groups, and siloxanoxy groups and each $R^1$ is independently selected from the group consisting of a hydrogen atom and organic groups, each $R^2$ is an independently selected hydrocarbon group; each Z is independently selected from the group consisting of silamino groups, siloxy groups, and siloxanoxy groups, and n=0, 1, 2, or 3.

2. The method of claim 1, where the (a) unsaturated group-functional organic compound or unsaturated group-functional organosilicon compound is selected from the group comprising:
   (1) styrene and styrene derivatives;
   (2) vinylsilane compounds;
   (3) siloxane compounds containing a vinyl group directly bonded to silicon;
   (4) epoxy-functional olefins;
   (5) diene compounds;
   (6) allyl compounds defined by $CH_2=CHCH_2X$ where X=halogen, alkoxy, or acyloxy;
   (7) vinyl-functional olefin compounds; and
   (8) acetylenic compounds.

3. A method according to claim 1 where in the hydro (acyloxy)-functional silicon compound (d), R is a substituent selected from the group consisting of $C_1$ to $C_6$ hydrocarbyl groups and $C_1$ to $C_6$ alkoxy groups and $R^1$ is a substituent selected from the group consisting of hydrogen atoms and saturated and unsaturated hydrocarbon groups that contain from 1 to 20 carbons and that may optionally contain at least 1 atom selected from the group consisting of oxygen, halogen, sulfur, and silicon.

4. A method according to claim 1, where the carboxylic acid compound is selected from the group consisting of carboxylic acids described by formula $$R^4COOH$$

carboxylic acid anhydrides described by formula $$(R^4CO)_2O,$$

and silyl carboxylate esters described by formula $$(R^4COO)_m SiR^5_{4-m};$$

in which $R^4$ is a substituent selected from the group consisting of hydrogen atoms and saturated and unsaturated hydrocarbon groups that contain from 1 to 20 carbons and that may optionally contain at least 1 atom selected from the group consisting of oxygen, halogen, sulfur, and silicon; each $R^5$ is a substituent independently selected from saturated and unsaturated hydrocarbon groups that contain from 1 to 20 carbons and that may contain at least 1 atom selected from the group consisting of oxygen, halogen, sulfur, and silicon; and m is 1, 2, 3, or 4; and the hydro(alkoxy)silane is described by formula $$HSiR^6{}_{3-k}(OR^7)_k$$

where each $R^6$ is independently selected $C_1$ to $C_6$ saturated and unsaturated hydrocarbyl groups, each $R^7$ is independently selected from saturated and unsaturated hydrocarbon groups that contain from 1 to 10 carbons and that may optionally contain at least 1 atom selected from the group consisting of oxygen, halogen, and silicon, and k=1, 2, or 3.

5. A method according to claim 1, where component (a) is an unsaturated group-functional organic compound.

6. A method according to claim 1, where component (a) is an unsaturated group-functional organosilicon compound.

7. A method according to claim 1, where component (b) is described by formula $HSiR^2{}_3$ is which $R^2$ is a hydrocarbyl selected from the group consisting of alkyl, aryl, and aralkyl.

8. A method according to claim 1, where Z is silamino.

9. A method according to claim 1, where Z is siloxy.

10. A method according to claim 1, where the weight ratio of component (d) to component (b) is 0.01:1 to 1:1.

11. A method according to claim 1, where the weight ratio of component (e) to component (b) is 0.01:1 to 1:1.

12. A method according to claim 1, where the reacting is conducted at a temperature in a range from 20° C. to 200° C.

* * * * *